United States Patent
Peters et al.

(10) Patent No.: US 7,364,898 B2
(45) Date of Patent: Apr. 29, 2008

(54) CUSTOMIZED MICRO-ARRAY CONSTRUCTION AND ITS USE FOR TARGET MOLECULE DETECTION

(75) Inventors: Lars-Erik Peters, Lafayette, CO (US); José Remacle, Malonne (BE); Konrad Beyreuther, Heidelberg (DE)

(73) Assignee: Eppendorf AG, Hamburg (DE)

( * ) Notice: Subject to any disclaimer, the term of this patent is extended or adjusted under 35 U.S.C. 154(b) by 261 days.

(21) Appl. No.: 10/839,780

(22) Filed: May 4, 2004

(65) Prior Publication Data

US 2005/0250109 A1 Nov. 10, 2005

(51) Int. Cl.
C12M 1/34 (2006.01)

(52) U.S. Cl. ............... 435/287.2; 435/7.1; 435/283.1; 435/287.1; 435/288.7; 436/518; 436/524; 436/528; 436/529; 436/530; 422/50; 422/68.1; 422/82.05

(58) Field of Classification Search ............... 436/518, 436/524, 528, 529, 530, 164; 435/4, 6, 7.1, 435/7.92, 7.94, 283.1, 287.1, 287.2, 288.7; 453/7.95; 422/50, 68.1, 82.05
See application file for complete search history.

(56) References Cited

U.S. PATENT DOCUMENTS

| | | | | |
|---|---|---|---|---|
| 5,158,869 A | * | 10/1992 | Pouletty et al. ............... | 435/7.9 |
| 5,700,637 A | | 12/1997 | Southern | |
| 5,700,921 A | * | 12/1997 | Westling et al. ............ | 536/22.1 |
| 6,083,763 A | * | 7/2000 | Balch .......................... | 436/518 |
| 6,316,186 B1 | * | 11/2001 | Ekins .............................. | 435/6 |
| 6,905,826 B2 | * | 6/2005 | Ferea et al. ..................... | 435/6 |
| 2001/0031468 A1 | * | 10/2001 | Chenchik et al. .............. | 435/6 |
| 2003/0003484 A1 | * | 1/2003 | Fagan ............................ | 435/6 |
| 2003/0003495 A1 | | 1/2003 | Delenstarr | |
| 2003/0027149 A1 | * | 2/2003 | Dorris et al. ................... | 435/6 |
| 2003/0198967 A1 | * | 10/2003 | Matson et al. ................. | 435/6 |
| 2004/0009506 A1 | | 1/2004 | Stephan et al. | |
| 2005/0053954 A1 | * | 3/2005 | Brennan et al. ............... | 435/6 |

FOREIGN PATENT DOCUMENTS

WO   WO 02/072889 A2   9/2002

OTHER PUBLICATIONS

Duggan et al. (1999) "Expression profiling using cDNA microarrays" *Nature Genetics Supplement* 21:10-14.
De Longueville et al. (2002) "Gene expression profiling of drug metabolism and toxicology markers using a low-density DNA microarray" *Biochemical Pharmacology* 64:137-149.

(Continued)

*Primary Examiner*—Long V. Le
*Assistant Examiner*—Melanie J. Yu
(74) *Attorney, Agent, or Firm*—Knobbe Martens Olson & Bear LLP

(57) ABSTRACT

The present invention relates to a detection and quantification method of different sets of target molecules (1, 3), being possibly present simultaneously in a biological sample by the use of a microarray present upon a solid support surface (6) and comprising different sets (A, B) of capture molecules (2, 4), present in different locations (8, 9) of the solid support surface (6).

16 Claims, 1 Drawing Sheet

OTHER PUBLICATIONS

Guo et al. (1994) "Direct fluorescence analysis of genetic polymorphisms by hybridization with oligonucleotide arrays on glass supports" *Nucleic Acids Research* 22:5456-5465.

Schena et al. (1996) "Parallel human genome analysis: microarray-based expression monitoring of 1000 genes" PNAS USA 93:10614-10619.

Schena et al. (1998) "Microarrays: biotechnology's discovery platform for functional genomics" *Tibtech* 16:301-306.

Yuen et al. (2002) "Accuracy and calibration of commercial oligonucleotide and custom cDNA microarrays" *Nucleic Acids Research* 30:1-9.

* cited by examiner

CUSTOMIZED MICRO-ARRAY CONSTRUCTION AND ITS USE FOR TARGET MOLECULE DETECTION

FIELD OF THE INVENTION

The present invention is related to a method and kit of detection, identification and/or quantification of multiple target molecules possibly present simultaneously in a sample.

BACKGROUND OF THE INVENTION AND STATE OF THE ART

Identification of multiple expressed genes, of organisms or of micro-organisms can be based on the presence in their genetic material of specific sequences. Identification and quantification of expressed genes is usually performed after reverse transcribing mRNA into its corresponding cDNA and detection of said cDNA via specific capture molecules present on or attached to micro-arrays. Detection of specific organisms can be performed easily by amplifying a particular sequence of their genomic DNA and then detecting and/or identifying these amplified sequences. Quantification of the target sequences bound to their specific capture molecules allows estimation of the amount of target molecules present in the initial sample. Preferably, appropriate control means are included and the necessary corrections made to take into account the efficiency of the different steps, such as the copying or amplification of target sequences and their capture via hybridization upon a micro-array.

Micro-arrays bearing arrays of nucleotide sequences are being produced mainly according to two methods. The first method, described in U.S. Pat. Nos. 5,510,270 and 5,700,637, is based on photolithographic in situ synthesis of capture molecules or sequences on a solid support. Photolithographic DNA synthesis uses rapid solid phase phosphoramidite chemistry. Positional and sequential control are achieved by a combination of 5'-photoprotected phosphoramidites, which can be activated by irradiation with light, and a set of masks containing holes at appropriate positions through which light can pass. Upon excitation, the photoprotecting groups present on partial oligonucleotide sequences, synthesized earlier during the process, are removed and the oligomers are extended by another nucleotide after adding the relevant monomer. Current coupling efficiencies impose an actual size limit of about 25 bases to these chips. Beyond this limit, incomplete products accumulate.

The photolithographic method results in the presence of short oligonucleotides on a support. Using this methodology, a gene or a gene sequence is identified by a series of capture sequences of the same species rather than by a unique sequence. To be able to control specific hybridization of a particular target sequence, it is necessary to perform for each sequence a control, the control sequence being identical to the initial sequence but for one base difference. The main advantage of the method is the possibility to miniaturize the thus obtained arrays or chips and to generate high-density arrays containing several thousands of capture sequences.

The second method is based on the chemical or enzymatic synthesis of capture sequences before mechanical deposition onto known specific locations of the array substrate. With this method, there is no restriction in the size of the sequences to be spotted, deposited or attached. One major advantage of the deposition technology, compared to the in situ synthesis approach, is its great versatility. This method allows production of micro-arrays or chips for virtually any molecule of interest including but not limited to nucleic acid sequences of any length, antibodies, lipids, carbohydrates, small chemical compounds, etc. Furthermore, the synthesis of sequences can be optimized, sequences can be purified, their quality checked before use and/or their concentration adjusted before coupling to the solid surface. However, one disadvantage of the method is that the process is time-consuming since each sequence has to be handled separately before spotting on the micro-array or chip, thereby limiting the size of the arrays.

The chemistry of a hybridization-to-oligonucleotide micro-array is clearly different from that of an array constructed with long DNA capture sequences or molecules. It has been observed that long specific capture sequences give much better binding of a complementary target sequence present in a solution or sample than their corresponding short fragments. In practice long polynucleotide capture sequences are used for direct binding of long polynucleotide target molecules or sequences. In a typical gene expression experiment, the capture sequences for cDNA binding contain 50 bases or more, for example 70 bases, or may even contain 600 bases or nucleotides.

When short oligonucleotides of 15-20 bases only are used as capture sequences (see e.g. U.S. Pat. No. 5,510,270) adequate detection, identification and/or quantification of long cDNAs is possible provided some modifications to the detection protocol. The RNA is first reverse transcribed into its corresponding cDNA by using a primer carrying a transcription start site for T7 RNA polymerase. This cDNA is then retranscribed in vitro into several RNA copies which are then cut into small pieces. These small RNA fragments are then used for hybridization on arrays bearing a series of capture sequences for each of these RNA fragments. Fragmentation is necessary to ensure sufficient access of the target RNA sequences to the very short capture sequences. Specific algorithms are required to adequately correlate the hybridization pattern of these different capture molecules with the original sequence(s) of the target DNA or mRNA.

A similar adaptation is made for the detection of double stranded DNA (dsDNA), which will preferentially re-associate in solution rather than being hybridized on capture sequences present on or attached to a solid substrate. Again the amplicons have to be retranscribed into RNA using a double amplification process performed with primer(s) bearing T3 or T7 sequences and then a retrotranscription with a RNA polymerase. These RNAs are cut into pieces of about 40 bases before being detected on an array (see e.g. example 1 of international patent application WO97/29212). The above technique was herein applied for the identification of the *Mycobacterium tuberculosis* rpoB gene, using capture nucleotide sequences of less than 30 nucleotides. The described method is complicated in the sense that it does not allow direct detection of amplicons resulting from genetic amplification reactions (such as PCR), but requires another cycle of reactions and copying of target sequences, which each introduce extra bias in the quantification of said target sequences.

Despite some disadvantages, the construction of micro-arrays via chemical synthesis and deposition of oligonucleotides or short polynucleotide sequences, is useful, since it is a fast and low-price process. In addition to that, the design of capture molecules or sequences can be easily adapted according to the requirements of the sequences to be analyzed or discriminated.

Capture molecules do not necessarily have to consist of nucleotide sequences. Target molecules may as well be antibodies, antigen, receptors or ligands to be detected or captured by binding to their respective corresponding counterparts (antibody, antigen, ligand, receptor, . . . ). The above list of examples is non-exhaustive.

A customer is not always served with standard micro-arrays even though these may allow detection of a large amount of different target molecules. He may want to detect target molecules that are not custom, or may want to refine the level of discrimination. There is thus an ever increasing demand for customized or semi-customized micro-arrays to which the customer can add, at his wish, some extra detection molecules. The basic or standard micro-array that is further customized possibly already contains many different capture molecules for well determined gene detection.

Standard micro-arrays can be constructed and delivered to many users which can then use them for detection of some well defined target genes beside other target genes which would change from one application to the other or from one user to the other.

AIMS OF THE INVENTION

In one embodiment, the present invention provides novel detection, identification and quantification methods and kit with standard micro-arrays that can be easily adapted for the specific needs of one or more particular customers for the detection of multiple target molecules.

One embodiment of the present invention allows a customer to detect in one particular experiment one set of new target molecules possibly changing from one experiment to the other beside a set of target molecules which are compatible with the capture molecules already bound to the surface of the solid support according to a micro-array, said detection of target molecules in both group being quantitative and related to their presence in the sample.

SUMMARY OF THE INVENTION

The present invention is related to a method of detection or quantification of different sets of target molecules (a first set and a second set of target molecules) being possibly present simultaneously in a biological sample; said method comprises the step of putting into contact these sets of target molecules with a (micro)array present on a solid support surface; said (micro)array comprising a first and a second set of capture molecules, present in different locations of the solid support surface.

In the method of the invention, the first set of capture molecules comprises at least 3 capture molecules which are specific of the first set of target molecules, and which fix directly the first set of target molecules by specific molecular recognition (preferably by hybridisation), and the second set of capture molecules comprises at least 3 capture molecules which are unrelated and have no direct affinity with the second set of target molecules (and with the first set of target molecules); the second set of capture molecules is able to fix the second set of target molecules through an adaptor molecule which allows a complementary binding between capture molecules and target molecules.

Furthermore, in the method of the invention a relative quantification of one set of target molecules compared to the other set of target molecules is obtained advantageously by a correction factor calculated through the use of at least one additional identical target molecule (able to bind first set of capture molecules and second set through an adaptor molecule) simultaneously quantified on both capture molecules sets.

The correction factor used in the method according to the invention could be obtained by the person skilled in the art by using a target of unknown concentration which is able to fix the two sets of capture molecules or by using internal standard having a known concentration added to the sample and submitted to the same pre-treatment (purification, amplification, copy) steps and the contact step with the target molecules to be detected and/or quantified. Said international standard of known concentration is also able to bind with the two sets of capture molecules.

Therefore, in order to allow a suitable quantification of the target present in one of the two sets of target molecules, the person skilled in the art can identify the ratio between the two signals resulting from binding upon two capture molecules in the two sets, said signal is obtained in order to allow the person skilled in the art to provide a correction factor used for the quantification of the other target molecules to be detected and quantified.

Another aspect of the present invention, is related to a detection and a quantification kit which comprises:
  a (micro)array set solid support surface comprising a first and a second set of capture molecules present in different locations of the support surface, wherein the first set of capture molecule comprises at least three different capture molecules being specific to the target molecules to be detected and quantified in a sample, said capture molecules of the first set being able to fix directly a first set of target molecules;
  and wherein the (micro)array solid support surface further comprises at different locations of the solid support surface, a second set of capture molecules comprising at least three capture molecules unrelated and having no direct binding affinity to a second set of target molecules (and also the first set of target molecules) to be detected and quantified and possibly present simultaneously in the sample with the first set of target molecules;
  one or more adaptor molecule(s) which allow specific binding of the target molecules of the second set onto the capture molecules of the second set and;
  a correction factor for one set of target molecules that allows to compare the amount of target molecules of the first set with the target molecules of the second set being in the sample.

Preferably, in the method and kit according to the invention, the capture molecules of the second set are totipotent capture molecules ("universal micro array" portion). Therefore, they are unrelated and having no direct binding affinity to complementary target molecules by their own, said binding being allowed only through adaptor molecules.

According to a first embodiment of the present invention, the detection and quantification is performed on the (micro)array, divided into at least two different arrays, presented on the same surface of the solid support. Each array comprises first and second set of capture molecules present in different locations of the support surface. Said at least two different arrays, comprising capture molecules of the first set for the detection of the same target molecules and each other different array comprising different second sets of capture molecules for the detection of other target molecules, being different from one array to another. This means that it is possible to obtain a specific similar detection on a first location of target molecules, and different detection pattern of other types of target molecules following binding of said target molecules upon capture molecules of different arrays through specific adaptor molecules. Said adaptor molecules being different from one array to another array.

According to a second embodiment of the present invention, the fixing of the target molecules upon the second set of capture molecules is performed by a consumer addition of adaptor molecules upon the solid support. This means that the arrays according to the invention are "semi-customised" arrays which could be used for obtaining a specific binding according to the request of the consumer for specific identifications of target molecules at specific locations of the micro-array surface.

According to a first aspect of the present invention, the target, capture and the adaptor molecules are or comprise nucleotide sequences. In said embodiment, the fixing of the target molecules upon the second set of capture molecules is therefore obtained by a sandwich hybridization between the capture molecules and the target molecules through adaptor molecules being or comprising also complementary nucleotide sequences.

Preferably said sandwich hybridization is obtained by adaptor molecules which comprise a first portion, which allows a hybridization by complementary base pairing with a specific terminal portion of the capture molecules and a second portion, which is specific for at least a portion of one or more target molecules.

The specific terminal portion of a capture molecule being a nucleotide sequence, means the 5' or 3' terminal portion which is not bound to the surface of the solid support.

According to another aspect of the present invention, the target and capture molecules are proteins and adaptor molecules are chimeric proteins or hybrid antibodies which allows a specific indirect binding between capture and target molecules. According to a preferred example, the target and capture molecules are respectively either antigens and antibodies (or hypervariable portions of said antibodies)
or antibodies (or portions) and antigens.

The invention also provides means to determine (to quantify) the amounts of the two sets of target molecules detected in the initial sample. The amount of the different target molecules is either relative to each other or is corrected into absolute values (pmoles).

Quantitative detection is corrected by a factor which allows comparable and simultaneously detection of all fixed target molecules (fixed to their capture molecules). More preferably, in the method according to the invention, the quantitative detection is corrected by a detection of at least one standard sequence(s) added to the (biological) sample and submitted to the same detection steps as target molecules. Said standard molecule(s) are detected on both sets of capture molecules present on the two locations of the solid support surface.

In another aspect of the invention, the fixation efficiency of target molecules on the two groups of capture molecules is corrected by a quantitative detection of at least one common target in both sets. In a more specific embodiment, the common target molecule is a housekeeping gene.

Preferably, 3 standards or 3 target molecules are detected and quantified on both sets of capture molecules, each of the target molecules being different in concentration by at least a factor 3.

In order to allow a specific binding between capture molecules and target molecules, through adaptor molecules the capture molecules of the second set comprise one or more terminal reactive chemical function(s) able to bind specifically to the adaptor molecules. Preferably, said terminal reactive chemical function is selected from the group consisting of aldehyde groups, epoxy groups, acrylate groups or a mixture thereof.

Preferably all capture molecules are attached to the solid support surface by a covalent bond or link to form a micro-array on the solid support surface. In a first embodiment of the invention, the second location of the surface contains capture molecules terminated by a reactive chemical function (such as an aldehyde group, an epoxide group or an acrylate group that may react with a NH2 group of the adaptor molecule.

To avoid sterical hindrance, the capture molecules are bound to the surface of the solid support through a spacer (or link) of a particular length. This spacer element or molecule may be a polymeric chain of at least 10 atoms, possibly branched and selected from the group consisting of polyethyleneglycol, polyaminoacids, polyacrylamides, polyaminosaccharides, polyglucides, polyamides, polyacrylates, polycarbonates, polyepoxides, poly-ester molecules or chains, or a mixture thereof Alternatively, part of the capture molecule may act as a spacer molecule. Preferably, the spacer molecule is at least 6.8 nm long. Possibly, the spacer molecule is a nucleotide sequence of between about 15 and about 1000 bases, preferably between about 30 and about 120 bases.

The method and kit of the invention are particularly suited for the simultaneous detection, identification and/or quantification of biological molecules of interest such as target polynucleotides or nucleotide sequences (possibly homologous sequences simultaneously present in a biological sample or test solution), wherein a basic multi-parametric micro-array is adapted according to a customer's needs. Preferably, the target molecules such as target polynucleotides or nucleotide sequences (e.g. genomic DNA or RNA sequences or amplicons), prior to detection, are multiplied (copy) and/or amplified (genetic amplification) with techniques that are standard in the art. Alternatively, the detection signal may be amplified with techniques well known to a person skilled in the art.

In the context of the present invention, the meaning of the terms "nucleic acid", "oligonucleotide", "array" or "micro-array", "nucleotide sequence", "target nucleic acid" or "target nucleotide sequences", "bind substantially", "hybridizing specifically to", "background", "quantifying" and the like is as described in the international patent application WO97/273 17, which is incorporated herein by reference in its entirety.

The meaning of the term "homologous sequence(s)" is as described in European patent EP 1266034, which is incorporated by reference herein in its entirety.

The term "solid support" for building micro-arrays in the present context is meant to comprise any type of solid material which can be physically handled to perform the necessary reactions like incubation of a test solution or sample possibly containing target molecules or copies of a target sequence. This solid support can be unique or can be a composite made of several materials, one of them being a substrate surface on which capture molecules or nucleotide sequences can be fixed or bound to yield a micro-array. Typical examples of substrates used in the field are polymers which may be functionalized (including submitted to the addition of a linker to their surface) in order to better fix the capture molecules. Said substrates or support surfaces on which the capture molecules are fixed or bound may be a porous or non porous support, may be smooth or rough and may be deposited or placed on top of another solid support, being made for example of glass or of plastic.

The terms "sample", "biological sample" or "test solution" are meant to comprise any (biological) sample or solution suspected to contain a target molecule. Said target molecule may be a (micro)organism or obtained from a (micro)organism or a component thereof (such as chloroplasts, mitochondries, genes, gene products, proteins, peptide, toxins, antigens, lipids, saccharides . . . )

In the context of the present invention, especially polynucleotides or nucleotide sequences specific to a (micro) organism or to a component (meat, bones, . . . ) thereof are being detected by the second set of capture molecules wherein target molecules are captured by a specific adaptor molecule. A test solution may be a solution containing PCR products (amplicon) of a (micro)organism or a component thereof.

In the present context the term "target molecule" may refer to a nucleotide sequence or polynucleotide, but also to a protein, a lipid, a saccharide etc. to be detected in a sample.

In the present context, a "capture molecule" may comprise a nucleotide sequence, but may as well comprise an antibody or hypervariable portion thereof (Fab, Fab2, etc.), an antigen or epitope thereof, a receptor, a ligand of a receptor, . . . specific for a target molecule and/or specific for an adaptor molecule.

In the context of the present invention, the term "adaptor" may refer to a polynucleotide sequence or polypeptide sequence (such as an antibody, chimeric molecule, etc.) which makes the link between a capture molecule and a target molecule.

The invention will be described in further details in the following examples and specific embodiments, by reference to the enclosed drawings. The examples, embodiments and drawings are not in any way intended to limit the scope of the invention as claimed, neither are the reference signs used.

BRIEF DESCRIPTION OF THE DRAWINGS

The FIG. 1 represents the surface of the solid support (6) in the form of an array (7), made of two sets of capture molecules (A, B) present in different locations (8, 9) of the solid support surface. The first set (A) is made of capture molecules (2) which are specific for the target molecules (1) whereas the second set (B) is made of capture molecules (4), unrelated to target molecules (3). One identical molecule (x) is simultaneously quantified on both sets (A, B) of capture molecules.

The FIG. 2 represents the surface of a glass slide covered with two "semi-customized" arrays (7', 7") according to the invention. In the first locations (8', 8"), the first set of capture molecules (A) is common on both arrays and they allow the detection of target molecules of the first group (1). However, on the second locations (9', 9"), the second sets of capture molecules (B, B') are different on both arrays and they allow the detection of different target molecules of the second group. One identical molecule (x) is simultaneously quantified on both sets (A, B-B') of capture molecules.

Figure 3:
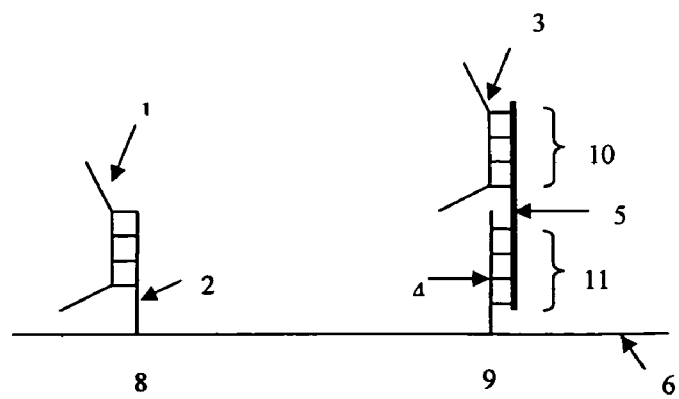

The FIG. 3 represents a solid support surface (6) according to the invention covered by two sets of capture molecules (2, 4) present in different locations of the solid support surface (8, 9). The first set of capture molecules (2) are specific for a first group of target molecules (1), while the second set of capture molecules is unrelated to a second group of target molecules (3), but can detect it through the use of a target (3) specific adaptor (5).

DETAILED DESCRIPTION OF THE INVENTION

The present invention is related to a method and kit which allows a detection and quantification of multiple target molecules (1, 3). Possible presented simultaneously in a sample by the detection after the fixation upon complementary capture molecules, present upon a solid support surface (6) according to an array (7).

Said surface (6) comprises at least two sets of capture molecules (2, 4), presented in different locations (8, 9) of the solid support surface (6), wherein a first set A comprising at least 3 different capture molecules (2) being specific for target molecules (1) to be detected, identified and/or quantified, said capture molecules being able to fix directly the target molecule 1; and wherein the second set B comprising at least 3 capture molecules (4), unrelated to other target molecules (3) to be detected and quantified and having no different affinity to fix the said target molecules (3), said second set of capture molecules (4) fixing the target molecules (3) through adaptor molecules (5). At least one identical molecule (x) is simultaneously quantified on both sets of capture molecules.

Figure 1:
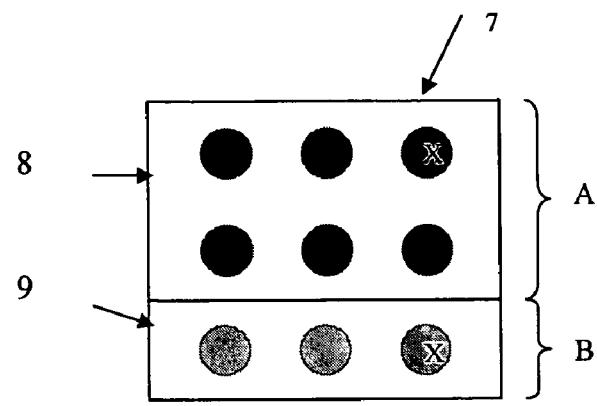
Figure 2:
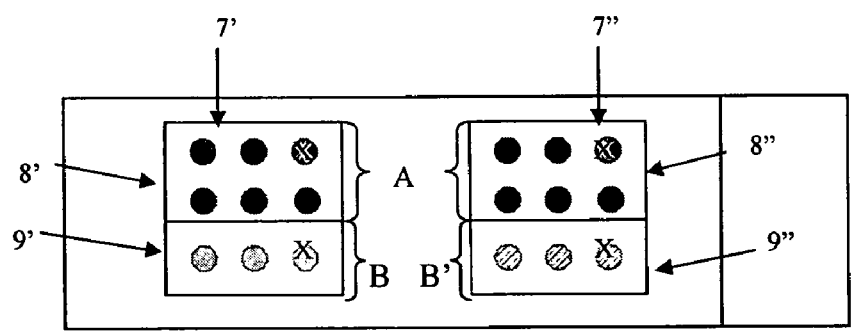

According to a preferred embodiment of the present invention described in the FIGS. 1 and 3, the capture molecules are presented on the solid support surface 6 in the form of an array (7, 7', 7"). As described in the FIG. 2, the detection can be performed by using a solid support surface, comprising at least two different micro-arrays (7', 7") present on the surface (6) of said solid support;

Said at least two arrays (7', 7") comprising capture molecules (2) of set A on first location (8', 8") for the detection of the same target molecules (1).

Furthermore, each array (7', 7") comprising also different sets (B, B') of capture molecules (4, 4') for the detection of target molecules (3, 3') being different from one array (7') to another (7"), said second set (B, B') of capture molecules (4, 4') being present on the different locations (9', 9") from the locations (8', 8") of the first set A.

According to the invention, this standard (micro-)array is adapted to detect, identify and/or quantify less common (other) target molecules (3) by adding to said standard support surface (6), that contains already capture molecules (2) for at least a first set of target molecules (1), adaptor molecules (5) that can bind to totipotent capture molecules (4), which can not directly bind to any of the target molecules (3) possibly present in a sample or a test solution. Said totipotent capture molecules (4) are already present (bound to the surface (6), on the standard micro-array (7) to customize. Preferably, said (totipotent) capture molecules (4) are nucleotide sequences such as DNA or RNA sequences, possibly with modified backbone.

Most preferably, attachment (fixation) to the support surface (6) of capture molecules (4) from the second set (B) does not lead to the complete detachment and/or inactivation of said first set (A) of capture molecules (2). Preferably said detachment and/or inactivation are kept as low as possible.

The standard micro-array or array (7) of the invention, prior to customization, thus contains two types of capture molecules (2, 4). The first type of capture molecules (2) is specific for a first group of target molecules (1), whereas the second type of capture molecules (4) are not specific for target sequences (1 or 3). They are totipotent, but can be made specific through binding of target-specific adaptor molecules (5).

In a preferred embodiment of the invention, totipotent capture molecules (4), adaptor molecules (5) and target molecules (3) are nucleotide sequences. Advantageously, the adaptor molecules (5) are specific to at least one part of the target polynucleotide (3) or of its copy, to allow its specific hybridization, detection, identification and/or quantification by indirect fixing upon capture molecules (4).

The preformed standard assays to be customized, also referred to as standard products (e.g. general chips, micro-arrays for the detection of cancer, mouse micro-arrays etc), are micro-arrays with capture molecules for the detection of a given number of well defined target molecules. The density of the capture nucleotide sequences bound to the solid support surface at a specific location is preferably greater than about 10 fmoles, preferably about 100 fmoles per $cm^2$ of solid support surface. The standard products may be low density or high density arrays. Low density arrays make use of a standard product with a limited number of capture molecules for a limited and selected number of target molecules. The micro-arrays and the standard product of the invention contain at least 5, 10, 50, 100, 1000 or 10000 spots of capture molecules per $cm^2$.

The micro-arrays of the invention can be adapted for the detection of additional target molecules at the request of the user, in conjunction with target molecules detected by the first set of capture molecules. The same array according to the invention can thus be used for the detection of a large number of different target molecules, the number of possible target molecules to be detected being at least 10, 20, 50, 100 or even 500 times larger than the number of capture molecules present.

The present invention further extends to tools and reagents needed to customize the standard product and needed for subsequent detection, identification and/or quantification. The present invention is for instance also related to the above-described adaptor molecules (5) that are used to secure recognition and specific binding of target molecules (3) (possibly present in a biological sample or test solution), to the second set (B) of capture molecules (4) that are not able to bind directly to the said target molecules (3) present in the sample.

The second set (B) of capture molecules (4) do not have a nucleotide sequence complementary to a nucleotide stretch of a target molecule (3) to be detected or its complement.

In normal working conditions these target molecules (3), being polynucleotides or nucleotide sequences, will not bind to the capture molecules (4) if preferably less than 10 subsequent complementary bases are present or normally less than 15 complementary bases are present. Preferably there will be less than 5, more preferably less than 3, complementary base pairings possible between the target molecule and the totipotent capture molecule. Most preferably, no complementary base pair binding at all should be possible between a target polynucleotide or nucleotide sequence and this totipotent capture molecule. Hybridization, as known by the person skilled in the art, is defined by the percentage of identity or similarity of two sequences and is further defined by the hybridization conditions used (e.g. stringent, less stringent or non-stringent conditions), being dependent mostly of the temperature and the salt concentration.

An embodiment of the invention concerns customizable micro-arrays and their construction, starting from one and the same standard product, to be used for the detection of, on one hand, identical and identified target molecules and, on the other hand, of non-identified and variable target molecules.

In an embodiment of the invention, the above-described adaptor molecules (5) contain a sequence (10) of at least 30 consecutive nucleotides complementary to the target molecule (3) to be identified or to its complement, also referred to as the target-specific part of the adaptor molecule, and a sequence (11) of at least 30 consecutive nucleotides specific for the totipotent capture molecules (4) on which the target molecules will be detected and/or quantified indirectly, also referred to as the target non-specific or target-unrelated part of the adaptor molecule.

In another embodiment, the target-specific parts (10) of the adaptor molecule will consist of nucleotide sequences of more than 50 or 70 bases and even more than 100 or 150 bases.

In a preferred embodiment of the invention, the portion of the capture molecule (4) that is recognized by the adaptor molecule (5) exists at the terminal end (the extremity which is not bound to the surface (6) of the solid support) of said capture molecule (4) or is at least close to this end. It is preferably not too close to the other part or extremity of the capture molecule (4), through which the capture molecule (4) is attached to the solid support surface (6).

In another embodiment of the invention, the totipotent capture molecule (4) contains a sequence recognized by the adaptor molecule (5) and a sequence not recognized by the adaptor molecule (5) and not recognized by a target molecule (3). Preferably the latter is a spacer sequence of at least about 20 or 30 bases, preferably at least about 50 or 70 bases, more preferably at least about 100 or 150 bases long or a sequence comprised between said parameters.

In a preferred embodiment, the indirect binding of target molecules, via specific adaptor molecules (5) bound to totipotent capture molecules (4), will be with the same efficiency as the direct binding on the specific capture molecules (2) of the first set (A) present on the standard micro-array product (7). In another embodiment of the invention, the amount of adaptor molecule (5) added in the sample solution is adjusted in order to provide an efficiency of binding of target molecules (1, 3) that is then identical or similar for both sets (A, B), i.e. for the direct and for the indirect binding of the target molecules (1, 3).

In another embodiment, the quantification of a target molecule (1, 3) being present in a sample will be performed with a correction through the use of internal specific known standard sequences that are added in a specific known amount to the sample. Some of these sequences molecules will be detected by direct binding on the first set (A) of capture molecules (2), while other sequences will be detected indirectly trough the use of the above-described adaptor molecules (5), both types of binding possibly being corrected by a coefficient that is different for the two sets (A, B).

In a particular embodiment of the invention, the same internal standard will be captured both in the first set (A) of capture molecules by direct hybridization and in the second set of totipotent capture molecules by the use of adaptor molecules (5).

In another embodiment, the coefficient of correction for efficiency of hybridization for both sets of target molecules is obtained by the use of at least 1 and preferably at least 3 common target molecules being detected in both sets of capture molecules. In still another preferred embodiment, the 3 common target molecules are chosen in the high, medium and low copy number of genes present in the sample. The difference in the relative amount of such genes being at least a factor of 3 and preferably being 10 or more.

In one embodiment, the correction factor is different from one molecule to the other of the same set. The correction factor is common for a subset of molecules and is different for another subset of molecules of the same set. In a particular embodiment the molecules are classified into different subset according to their concentration and the factor of correction applied is different.

Quantification of target molecule like genes or their product (mRNA or protein) present in a sample is best performed using 3 different scanning settings in the array scanner (e.g. for the Packard array scanner settings used for the photomultiplier are 50, 70 and 100). The use of 3 settings and 3 targets or 3 internal standards present at different amounts, allows correction for efficiency of binding of both sets of target molecules in the 3 different scanning settings.

According to an embodiment of the invention, the efficiency of indirect binding of target molecules (3) on capture molecules (4) through adaptor molecules (5) is similar or identical to the direct binding of target molecules (1) on capture molecules (2) of at least about 100 or 150, more preferably at least about 200 or 300 and more preferably at least about 400 or 500 bases long.

In an embodiment of the invention, the micro-array contains capture molecules (2) of at least about 100 or 150 bases, more preferably at least about 200 or 300 bases and most preferably at least about 400 or 500 bases long for the direct capture of target molecules (1) to be detected in a biological sample or test solution.

In another embodiment, the capture molecules of both sets (A, B) are composed of a non-specific or unrelated sequence (spacer) being at least about 20 or 30 bases long, preferably at least about 50 or 70 bases long and still more preferably about 100 or 150 bases long, being attached to the support surface, and further at their terminal end a sequence specific either for the target molecule (1) or target sequence to be detected (in the case of direct binding) or for the adaptor molecule (5) (in the case of indirect binding). The specific or adaptor-specific part (11) of the capture molecules is at least 10 or 15 bases long, more preferably more than about 20 or 30 and even more preferably more than about 40 or 50 bases long. The length of the specific sequence of the capture nucleotide sequences (2) able to hybridize with the corresponding target nucleotide sequences may be comprised between about 10 and about 60 bases, more preferably between about 20 and about 30 bases. "About" in this context means that it is possible to have 1, 2, 3 to up to 5 nucleotides more or less than being mentioned.

In a particular embodiment of the invention, the capture molecules of the second set (B) are synthesized by PCR, using as template a common sequence. One primer has a floating sequence which differs from one capture sequence to the other and is used for the recognition of the adaptor molecule (5).

The arrays or micro-arrays (7,7',7") of the invention are highly suited for detection and/or quantification of genes expressed by cells, possibly after copying the target gene sequences at least in part into a cDNA strand and hybridization of the cDNA onto specific capture molecules provided according to the invention.

The method of the invention is particularly suited for the detection of sequences which are homologous to each other. Discrimination between homologous or nearly identical sequences is possible via the use of small or short specific sequences. For instance, the target-specific part of the capture molecules of the first group (A) or of the adaptor molecule (5), used to discriminate homologous target nucleotide sequences (1), may be between about 15 and about 50 bases long. The percentage of homology is preferably higher than about 40% or 50%, preferably higher than about 60%, 65% or 70%, more preferably higher than about 75%, 80%, 85% or 90%.

The method of the invention may even allow discrimination between target sequences that differ in one or a few nucleotides only and that thus contain one or a few SNPs (single nucleotide polymorphisms).

Advantageously, the method and arrays of the invention can be used for the identification and/or quantification of DNA sequences, single or double stranded sequences, either obtained directly from an organism or part thereof—i.e. without any prior amplification step—or, alternatively, after amplification of part of its genomic DNA or RNA. Amplification of target sequences may be achieved via any method known in the art, including but not limited to PCR, LCR, NASBA, rolling circle or any other method which allows the production of a rather reliable copy of the given sequence. One or more (PCR) primers or primer sets may be used in the genetic amplification procedure. Primers may be universal primers, consensus primers and/or type-specific primers. Possibly, a kit according to the invention may comprise chambers wherein the detection for the presence of any amplified sequences of (micro)organisms and the genetic amplification are performed in one and the same chamber. The means for a genetic amplification of target nucleotide sequences obtained from said (micro)organisms may be provided with the kit of the invention.

The amplified nucleotide sequence may be mRNA that is first retrotranscribed into cDNA, possibly using the same primer pair for retrotranscription and amplification.

Possibly, the presence of any amplified sequence is firstly detected during the genetic amplification cycles and thereafter identified on the array.

Detection of the target molecules captured on the micro-array can be done via any physical or chemical detection method known in the art including but not limited to the use of fluorescence marking, colorimetry, bioluminescence, chemiluminescence, electric, surface plasmon resonance, electromagnetic signals, . . . . Reading and interpretation of the capture or hybridization signal is enhanced by the fact that the capture molecules are linked to well-defined locations of the solid support.

The (insoluble) solid support or the substrate for the construction of the micro-array according to the invention preferably is selected from the group consisting of glasses, electronic devices, silicon supports, silica, metals or mixture thereof prepared in a format selected from the group of slides, discs, gel layers and/or beads. Beads are considered as arrays for as long as they have characteristics which allow to differentiate them from each other, so that identification of the beads is correlated with the identification of a given capture molecule and so of the target sequence. The above examples are not exhaustive.

In an embodiment of the invention, detection, identification and/or quantification of captured target sequences is facilitated by the use of an apparatus comprising at least a detection and/or quantification device to detect and/or quantify a signal formed at the location where a target molecule or component from a (micro)organism is captured on the array, possibly a reading device for information recorded upon a surface of said solid support, a computer program for recognizing the discrete regions bearing the bound target molecules upon its corresponding capture molecules and their locations, possibly a quantification program of the signal present at the locations and a program for correlating the presence of the signal at these location with the diagnostic and/or the quantification of the said (micro)organism or component. The present invention extends to an apparatus adapted for these purposes and able to read the micro-array of the invention and interpret its results.

The present invention further extends to the use of a customized array in a kit or detection method for the detection, identification and/or quantification of a mixture of biological molecules from a first and second set of target molecules. These target molecules may belong to different groups, sub-groups or sub-sub-groups of components or (micro)organisms. In an embodiment of the invention, the first set of capture molecules may be specific for individual target components or their sub-groups, whereas the second group is then specific for all the components of the group or vice versa.

The method and kit of the invention may be used for the detection of any kind of (micro)organism or any component thereof. Examples of (micro)organisms and components thereof include but are not limited to *Staphylococci* species selected from the group consisting of *S. aureus, S. epidermidis, S. saprophyticus, S. hominis* and/or *S. haemolyticus*, samples belonging to the *Mycobacteria* genus, sequences which belongs to the MAGE family or the HLA-A family, G coupled receptors, dopamine receptors, choline receptors, histamine receptors, members of the cytochrome P450 family, GRAM+ or GRAM-family bacteria.

One may target groups, sub-groups or individual target molecules or target sequences corresponding to families, genus, species, subtypes or individual organisms. Preferably, the families, genus, species, subtypes or individuals are bacteria such as those selected from the groups consisting of *Staphylococcus, Enterococcus, Streptococcus, Haemolyticus, Pseudomonas, Campylobacter, Enterobacter, Neisseria, Proteus, Salmonella, Simonsiella, Riemerella, Escherichia, Neisseria, Meningococcus, Moraxella, Kingella, Chromobacterium* and *Branhamella*. The above list is not-exhaustive.

EXAMPLES

Example 1

Construction of a Micro-Array having Target-Specific Capture Molecules and Target-non Specific Capture Molecules and Detection of Target Molecules through the use of a Specific Adaptor Molecule of 60 Bases Functionalization of the Glass Support The glass slides are functionalized for the presence of aldehydes according to the method described in European patent application EP1184349.

Fixation of Target-Specific (set A) and Target-non Specific Capture Molecules (set B−) on the Support The specific capture molecules are directed against 59 genes as described by Delongueville et al 2002 (Biochem. Pharmacol. 64:137-149). They target 59 toxicologically relevant genes in the Rat Hepatochip dualchip (Eppendorf, Hamburg, Germany). Three target-unrelated capture molecules are synthesized and spotted on the array. These 3 capture molecules are synthesized by PCR amplification from a cloned sequence of plant inserted into a plasmid. The 3 target molecules which are fixed through an adaptor on theses target unrelated capture molecules are simultaneously fixed on 3 target specific capture molecules. Since 3 target molecules are simultaneously quantified on both capture molecule sets, they will allow correction for the quantification of the target molecules.

The PCR sense primers that were used are the following:

```
PALFAS1 for sequence 1:              (SEQ ID NO:1)
5'-gcatggatgttgctctcgcgtagacgactggatggctagttactgct ctg-3'

PALUCP21 for sequence 2:             (SEQ ID NO:2)
5'-agtacgtcgacagacttagtcctgaagctcgatggctagttactgct ctg-3'

PALL191 for sequence 3:              (SEQ ID NO:3)
5'-ggctgatcatgtactccaaggtttgttatcgatggctagttactgct ctg-3'
```

The sense primers comprise 30 floating bases at the 5' end (bold) followed by 20 bases specific for the insert.

The antisense primer was common for the 3 PCR reactions. It is aminated at the 5' end and is specific for the insert.

```
PAL2:                                (SEQ ID NO:4)
5'-Amine-atgagtttcaagatttcaacag-3'
```

The sequences of the 3 capture molecules are the following:

```
TPALFAS:                             (SEQ ID NO:5)
5'Amine-
atgagtttcaagatttcaacatgagtttcaagatttcaacagcttctgat gttttccttgaagagattaagcccaaggagtttacatcttgattgtgttg ttcagcactttgaacatggttggtcactggattggctaaaaattgaagtt cagagcagtaactagccatccagagcagtaactagccatccagtcgtcta cgcgagagcaacatccatgc-3'

TPALUCP2:                            (SEQ ID NO:6)
5'Amine-
atgagtttcaagatttcaacatgagtttcaagatttcaacagcttctgat gttttccttgaagagattaagcccaaggagtttacatcttgattgtgttg ttcagcactttgaacatggttggtcactggattggctaaaaattgaagtt cagagcagtaactagccatccagagcagtaactagccatcgagcttcagg actaagtctgtcgacgtact-3'

TPALL19:                             (SEQ ID NO:7)
5'Amine-
atgagtttcaagatttcaacatgagtttcaagatttcaacagcttctgat gttttccttgaagagattaagcccaaggagtttacatcttgattgtgttg ttcagcactttgaacatggttggtcactggattggctaaaaattgaagtt cagagcagtaactagccatccagagcagtaactagccatcgataacaaac cttggagtacatgatcagcc-3'
```

A negative control consist of a capture molecule of identical length comprising a 30 bases random sequence which is not recognized by an adaptor present in the solution.

The capture molecules are diluted in spotting solution (EAT Namur, Belgium). The two sets of capture molecules are spotted with an arrayer using plain pins on spatially separated locations of the support. The slides are dried 1 h at room temperature. The slides are washed 2 times 2 min with washing buffer and 3 times with water. The slides are kept at 4° C. until use.

DETECTION OF TARGET cDNA ON A CUSTOMIZED MICRO-ARRAY OF THE INVENTION

The surface of the support containing the capture molecules of the first and second sets are surrounded with a hybridization frame which delimits the surface of the support being in contact with the solution containing the target molecules. The array is first incubated for 30 min at 55° C. with 3 different synthetic adaptor molecules. The adaptor molecules are polynucleotides of about 60 bases. They contain 30 bases complementary to the capture molecules and 30 bases complementary to the target cDNA sequences. The 3 target cDNA are FAS (Accession No: U03470, incorporated by reference herein), UCP2 (Accession No: AB010743, incorporated by reference herein) and L19 (Accession No: J02650, incorporated by reference herein).

The sequences of the 3 adaptor molecules are the following:

AFAS30: (SEQ ID NO:8)
5'-ataaagttttgggctgctgtgtggcaatgcgcatggatgttgctctc gcgtagacgactg-3'

AUCP230: (SEQ ID NO:9)
5'-atgccattgtcaactgtactgagctggtgaagtacgtcgacagactt agtcctgaagctc-3'

AL1930: (SEQ ID NO:10)
5'-cgtcctccgctgtggtaaaaagaaggtgtgggctgatcatgactcc aaggtttgttatc-3'

The sequences complementary to the capture molecules are indicated in bold.

The adaptor molecules are obtained by chemical synthesis (Eurogentec, Liege, Belgium). After incubation, the array is washed with SSC2× solution. The array is then incubated with biotinylated cDNA from rat liver as explained here above (Delongueville et al. 2002). After hybridization with the biotinylated target cDNA, the arrays are incubated with anti-Cyanine antibody (Jackson ImmunoResearch, Cy3: ref.-200.162.096, Cy5: ref.-200.172.096) diluted 1/1000 in B1 buffer containing 0.01% blocking agent. The biochips are then washed 4 times during 2 min with B1 buffer. The biochips are dried at room temperature and scanned with GMS418 ScanArray (General Scanning). After digitalization of the picture, the imagene software (Biodiscovery, Marina Del Rey, USA) is used in order to delimitate the spot surface, integrate the signal for each spot, subtract the local background around each spot, identify the localization of the spots and correlate the localization with the identity of the target. The quantification of the target present in the sample is obtained essentially as described here above (Delongueville et al. 2002). The quantification of target molecules from both sets are corrected in order to determine their amount in the initial sample used in the analysis. Correction is obtained through the use of the 3 common target cDNAs (FAS, UCP2 and L19 described above) simultaneously quantified on both capture molecule sets.

Example 2

Construction of a Micro-Array having Target-Specific Capture Molecules and Target-non Specific Capture Molecules and Detection of Target Molecules through the use of a Specific Adaptor Molecule of 80 Bases The experiment is performed as in example 1. The adaptor molecules used for the detection of the 3 target cDNA are polynucleotides of 80 bases. They contain 30 bases complementary to the capture molecules (bold) and 50 bases complementary to the target cDNA sequences.

The sequences of the 3 adaptor molecules are the following:

AFAS50: (SEQ ID NO:11)
5'-
ataaagttttgggctgctgtgtggcaatgcagaggcaaagagaaggaact gcatggatgttgctctcgcgtagacgactg-3'

AUCP250: (SEQ ID NO:12)
5'-
atgccattgtcaactgtactgagctggtgacctatgacctcatcaaagat agtacgtcgacagacttagtcctgaagctc-3'

AL1950: (SEQ ID NO:13)
5'-
cgtcctccgctgtggtaaaaagaaggtgtggttggaccccaatgaaacca ggctgatcatgtactccaaggtttgttatc-3'

Example 3

Construction of a Micro-Array having Target-Specific Capture Molecules and Target-non Specific Capture Molecules and Detection of Target Molecules and Internal Standards through the use of a Specific Adaptor Molecule of 60 Bases The experiment is performed as in example 1 with the detection of 3 common target molecules on both sets of capture molecules. The micro-array also contains 3 internal-standard specific capture molecules in set A (RBCL, CAB10B, rubisco activase). Three additional target-unrelated capture molecules are used for correction of hybridization efficiency. They are used to capture adaptor molecules partially complementary to the internal standard cDNA.

These 3 new target-unrelated capture molecules are synthesized by PCR amplification from a cloned sequence of plant inserted into a plasmid. The floating sequences of 30 bases at the 5' end of the primers differ from example 1.

The following sense primers were used:

PALRBCL1 for sequence 1: (SEQ ID NO:14)
5'-tctgttcccttacgactcgataagagctctgatggctagttactgct ctg-3'

PALCAB1 for sequence 2: (SEQ ID NO:15)
5'-actcttgctgaggctattcaaggcggcatcgatggctagttactgct ctg-3'

PALRUBI1 for sequence 3: (SEQ ID NO:16)
5'-atacagttcaatcgccgagtctacgcggtagatggctagttactgct ctg-3'

Again, the sense primers comprise 30 floating bases at the 5' end (bold) followed by 20 bases specific for the insert.

The antisense primer is the same as in example 1 (SEQ ID NO:4).

The sequences of the 3 capture molecules used for the 3 internal standards are the following:

```
TPALRBCL:                                    (SEQ ID NO:17)
5'Amine-
atgagtttcaagatttcaacatgagtttcaagatttcaacagcttctgat gttttccttgaagagattaagcccaaggagtttacatcttgattgtgttg ttcagcactttgaacatggttggtcactggattggctaaaaattgaagtt cagagcagtaactagccatccagagcagtaactagccatcagagctctta tcgagtcgtaagggaacaga-3'

TPALCAB:                                     (SEQ ID NO:18)
5'Amine-
atgagtttcaagatttcaacatgagtttcaagatttcaacagcttctgat gttttccttgaagagattaagcccaaggagtttacatcttgattgtgttg ttcagcactttgaacatggttggtcactggattggctaaaaattgaagtt cagagcagtaactagccatccagagcagtaactagccatcgatgccgcct tgaatagcctcagcaagagt-3'

TPALRUBI:                                    (SEQ ID NO:19)
5'Amine-
atgagtttcaagatttcaacatgagtttcaagatttcaacagcttctgat gttttccttgaagagattaagcccaaggagtttacatcttgattgtgttg ttcagcactttgaacatggttggtcactggattggctaaaaattgaagtt cagagcagtaactagccatccagagcagtaactagccatctaccgcgtag actcggcgattgaactgtat-3'
```

The 3 internal standard cDNA are RBCL (Accession No: L14403, incorporated by reference herein), CAB10B (Accession No: M32606, incorporated by reference herein) and *Lycopersicon pennellii* rubisco activase (Accession No: AF037361, incorporated by reference herein).

The sequences of the 3 adaptor molecules for the 3 internal standards are the following:

```
ARBCL30:                                     (SEQ ID NO:20)
5'-gtagcttacccttagacctttttgaagaatctgttcccttacgact cgataagagctct-3'

ACAB30:                                      (SEQ ID NO:21)
5'-ccaccacatctgctactgcagtgctgaatgactcttgctgaggctat tcaaggcggcatc-3'

ARUBI30:                                     (SEQ ID NO:22)
5'-gacggcttctacattgccctgctttcatgatacagttcaatcgccg agtctacgcggta-3'
```

Three internal standards are added at concentration of x,x and x. The relative binding efficiency of both sets of capture molecules are calculated at the 3 scanner settings and used for correction of the target detection in both sets of capture molecules. The correction is performed at each scanner setting for gene which quantification is linear.

The part of the adaptor molecule that is complementary to the capture molecule is indicated in bold.

The adaptor molecules are obtained by chemical synthesis. For the rest, the experiment is performed as in example 1 and signals obtained on the internal standard capture molecules are used for correction of hybridization efficiency between the target-specific and target-non specific capture molecules.

---

What is claimed is:

1. A method for a detection and quantification of a first set and a second set of target molecules upon at least one micro-array, said method comprising:

provi ding a micro-array formed upon a solid support surface, comprising a first set and a second set of capture molecules, present in different locations of the solid support surface, wherein the first set of capture molecules is made of at least 3 capture molecules which are specific of the first set of target molecules and bind directly the first set of target molecules by specific molecular recognition, and wherein the second set of capture molecules is made of at least 3 capture molecules which are unrelated with the second set of target molecules and have no direct binding affinity with the second set of target molecules, the second set of capture molecules being capable of binding to adaptor molecules which bind to the second set of target molecules, contacting said first set of target molecules and said second set of target molecules with the first set of capture molecules and the second set of capture molecules, wherein said first set of target molecules and said second set of target molecules comprise at least one identical target molecule which is capable of binding to the fist set of capture molecules and to the adaptor molecules which bind to the second set of target molecules, wherein said contacting of said first set of target molecules with the first set of capture molecules is a direct assay, detecting specific signal(s) resulting from a binding of the target molecules to the first set and second set of capture molecules, and performing a relative quantification of the first set of target molecules compared to the second set of target molecules using a correction factor calculated from a ratio between a first signal resulting from the binding of said identical target molecule on the first set of capture molecules and a second signal resulting from the binding of the same identical target molecule on the second set of capture molecules.

2. The method according to claim 1, wherein the relative quantification of the target molecules belonging to the first or second set are classified into at least 2 sub-sets of target molecules and are corrected according to different correction factors.

3. The method according to claim 2, wherein the different correction factors are obtained by scanning the micro-array different scanning settings used for a photomultiplier of a detection scanner.

4. The method according to claim 2, wherein the sub-sets of target molecules correspond to different concentrations of target molecules.

5. The method according to claim 1, wherein at least one standard molecule of known concentration is added to the first and second set of target molecules and submitted to the same detection step as the target molecules and wherein the micro-array further comprises a first set and a second set of capture molecules which are capable of binding to said at least one standard molecule and wherein a relative quantification of the first set of target molecules compared to the second set of target molecules is performed using a second correction factor calculated from a ratio between a first signal resulting from the binding of said standard molecule on the first set of capture molecules and a second signal resulting from the binding of the same standard molecule on the second set of capture molecules.

6. The method according to claim 1, wherein the capture molecules of the second set are totipotent capture molecules.

7. The method according to claim 1, wherein the detection and quantification is performed on at least two micro-arrays present on the surface of the solid support; wherein said at least two micro-arrays comprise capture molecules of a first set for the detection and quantification of the same first set of target molecules; and each micro-array comprises different sub sets of capture molecules for the detection and quantification of target molecules that are different from one microarray to another microarray.

8. The method according to the claim 1, wherein the adaptor molecules are added by a consumer to the first set and second set of target molecules and wherein the mixture of target and adaptor molecules is contacted with the microarray.

9. The method according to the claim 1, wherein the molecules selected from the group consisting of target, capture and adaptor molecules are nucleotide sequences.

10. The method according to the claim 9, wherein the binding of the target molecules upon the second sub set(s) of capture molecules is obtained by a sandwich hybridization between the capture molecules, and the target molecules through the adaptor molecules.

11. The method according to the claim 10, wherein the adaptor molecule comprises a first portion, which allows an hybridization by complementary base pairing with a specific terminal portion of the capture molecule, and wherein the adaptor molecule comprises a second portion which is specific for at least a portion of one or more target molecules of the second set of target molecules.

12. The method according to the claim 1, wherein the target molecules and capture molecules are proteins and wherein the adaptor molecules are chimeric proteins or hybrid antibodies.

13. The method according to the claim 1, wherein the target molecules are antigens and the capture molecules antibodies or hypervariable portions of said antibodies or wherein the target molecules are—antibodies or hypervariable portions of said antibodies and the capture molecules are antigens.

14. The method according to the claim 1, wherein the capture molecules of the second set comprise a terminal reactive chemical function able to bind specifically to adaptor molecules.

15. The method according to claim 14, wherein said terminal reactive chemical function is selected from the group consisting of aldehyde groups, epoxy groups, and acrylate groups or is a mixture thereof.

16. The method according to claim 1, wherein said first set and said second set of target molecules are present simultaneously in a biological sample.

* * * * *

SEQUENCE LISTING

```
<160> NUMBER OF SEQ ID NOS: 22

<210> SEQ ID NO 1
<211> LENGTH: 50
<212> TYPE: DNA
<213> ORGANISM: Artificial Sequence
<220> FEATURE:
<223> OTHER INFORMATION: PALFAS1 sense primer

<400> SEQUENCE: 1
gcatggatgt tgctctcgcg tagacgactg gatggctagt tactgctctg          50

<210> SEQ ID NO 2
<211> LENGTH: 50
<212> TYPE: DNA
<213> ORGANISM: Artificial Sequence
<220> FEATURE:
<223> OTHER INFORMATION: PALUCP21 sense primer

<400> SEQUENCE: 2
agtacgtcga cagacttagt cctgaagctc gatggctagt tactgctctg          50

<210> SEQ ID NO 3
<211> LENGTH: 50
<212> TYPE: DNA
```

<213> ORGANISM: Artificial Sequence
<220> FEATURE:
<223> OTHER INFORMATION: PALL191 sense primer

<400> SEQUENCE: 3
ggctgatcat gtactccaag gtttgttatc gatggctagt tactgctctg         50

<210> SEQ ID NO 4
<211> LENGTH: 22
<212> TYPE: DNA
<213> ORGANISM: Artificial sequence
<220> FEATURE:
<223> OTHER INFORMATION: PAL2 antisense primer
<220> FEATURE:
<221> NAME/KEY: misc_feature
<222> LOCATION: (1)..(1)
<223> OTHER INFORMATION: aminated a

<400> SEQUENCE: 4
atgagtttca agatttcaac ag         22

<210> SEQ ID NO 5
<211> LENGTH: 220
<212> TYPE: DNA
<213> ORGANISM: Artificial sequence
<220> FEATURE:
<223> OTHER INFORMATION: TPALFAS capture molecule
<220> FEATURE:
<221> NAME/KEY: misc_feature
<222> LOCATION: (1)..(1)
<223> OTHER INFORMATION: aminated a

<400> SEQUENCE: 5
atgagtttca agatttcaac atgagtttca agatttcaac agcttctgat gttttccttg         60
aagagattaa gcccaaggag tttacatctt gattgtgttg ttcagcactt tgaacatggt        120
tggtcactgg attggctaaa aattgaagtt cagagcagta actagccatc cagagcagta        180
actagccatc cagtcgtcta cgcgagagca acatccatgc                              220

<210> SEQ ID NO 6
<211> LENGTH: 220
<212> TYPE: DNA
<213> ORGANISM: Artificial sequence
<220> FEATURE:
<223> OTHER INFORMATION: TPALUCP2 capture molecule
<220> FEATURE:
<221> NAME/KEY: misc_feature
<222> LOCATION: (1)..(1)
<223> OTHER INFORMATION: aminated a

<400> SEQUENCE: 6
atgagtttca agatttcaac atgagtttca agatttcaac agcttctgat gttttccttg         60
aagagattaa gcccaaggag tttacatctt gattgtgttg ttcagcactt tgaacatggt        120
tggtcactgg attggctaaa aattgaagtt cagagcagta actagccatc cagagcagta        180
actagccatc gagcttcagg actaagtctg tcgacgtact                              220

<210> SEQ ID NO 7
<211> LENGTH: 220
<212> TYPE: DNA
<213> ORGANISM: Artificial sequence
<220> FEATURE:
<223> OTHER INFORMATION: TPALL19 capture molecule
<220> FEATURE:
<221> NAME/KEY: misc_feature
<222> LOCATION: (1)..(1)
<223> OTHER INFORMATION: aminated a

<400> SEQUENCE: 7

```
atgagtttca agatttcaac atgagtttca agatttcaac agcttctgat gttttccttg      60
aagagattaa gcccaaggag tttacatctt gattgtgttg ttcagcactt tgaacatggt     120
tggtcactgg attggctaaa aattgaagtt cagagcagta actagccatc cagagcagta     180
actagccatc gataacaaac cttggagtac atgatcagcc                           220
```

<210> SEQ ID NO 8
<211> LENGTH: 60
<212> TYPE: DNA
<213> ORGANISM: Artificial sequence
<220> FEATURE:
<223> OTHER INFORMATION: AFAS30 adaptor molecule

<400> SEQUENCE: 8

```
ataaagtttt gggctgctgt gtggcaatgc gcatggatgt tgctctcgcg tagacgactg      60
```

<210> SEQ ID NO 9
<211> LENGTH: 60
<212> TYPE: DNA
<213> ORGANISM: Artificial sequence
<220> FEATURE:
<223> OTHER INFORMATION: AUCP230 adaptor molecule

<400> SEQUENCE: 9

```
atgccattgt caactgtact gagctggtga agtacgtcga cagacttagt cctgaagctc      60
```

<210> SEQ ID NO 10
<211> LENGTH: 60
<212> TYPE: DNA
<213> ORGANISM: Artificial sequence
<220> FEATURE:
<223> OTHER INFORMATION: AL1930 adaptor molecule

<400> SEQUENCE: 10

```
cgtcctccgc tgtggtaaaa agaaggtgtg ggctgatcat gtactccaag gtttgttatc      60
```

<210> SEQ ID NO 11
<211> LENGTH: 80
<212> TYPE: DNA
<213> ORGANISM: Artificial sequence
<220> FEATURE:
<223> OTHER INFORMATION: AFAS50 adaptor molecule

<400> SEQUENCE: 11

```
ataaagtttt gggctgctgt gtggcaatgc agaggcaaag agaaggaact gcatggatgt      60
tgctctcgcg tagacgactg                                                  80
```

<210> SEQ ID NO 12
<211> LENGTH: 80
<212> TYPE: DNA
<213> ORGANISM: Artificial sequence
<220> FEATURE:
<223> OTHER INFORMATION: AUCP250 adaptor molecule

<400> SEQUENCE: 12

```
atgccattgt caactgtact gagctggtga cctatgacct catcaaagat agtacgtcga      60
cagacttagt cctgaagctc                                                  80
```

<210> SEQ ID NO 13
<211> LENGTH: 80
<212> TYPE: DNA

```
<213> ORGANISM: Artificial sequence
<220> FEATURE:
<223> OTHER INFORMATION: AL1950 adaptor molecule

<400> SEQUENCE: 13
cgtcctccgc tgtggtaaaa agaaggtgtg gttggacccc aatgaaacca ggctgatcat    60
gtactccaag gtttgttatc                                                80

<210> SEQ ID NO 14
<211> LENGTH: 50
<212> TYPE: DNA
<213> ORGANISM: Artificial sequence
<220> FEATURE:
<223> OTHER INFORMATION: PALRBCL1 sense primer

<400> SEQUENCE: 14
tctgttccct tacgactcga taagagctct gatggctagt tactgctctg               50

<210> SEQ ID NO 15
<211> LENGTH: 50
<212> TYPE: DNA
<213> ORGANISM: Artificial sequence
<220> FEATURE:
<223> OTHER INFORMATION: PALCAB1 sense primer

<400> SEQUENCE: 15
actcttgctg aggctattca aggcggcatc gatggctagt tactgctctg               50

<210> SEQ ID NO 16
<211> LENGTH: 50
<212> TYPE: DNA
<213> ORGANISM: Artificial sequence
<220> FEATURE:
<223> OTHER INFORMATION: PALRUBI1 sense primer

<400> SEQUENCE: 16
atacagttca atcgccgagt ctacgcggta gatggctagt tactgctctg               50

<210> SEQ ID NO 17
<211> LENGTH: 220
<212> TYPE: DNA
<213> ORGANISM: Artificial sequence
<220> FEATURE:
<223> OTHER INFORMATION: TPALRBCL capture molecule
<220> FEATURE:
<221> NAME/KEY: misc_feature
<222> LOCATION: (1)..(1)
<223> OTHER INFORMATION: aminated a

<400> SEQUENCE: 17
atgagtttca agatttcaac atgagtttca agatttcaac agcttctgat gttttccttg    60
aagagattaa gcccaaggag tttacatctt gattgtgttg ttcagcactt tgaacatggt   120
tggtcactgg attggctaaa aattgaagtt cagagcagta actagccatc cagagcagta   180
actagccatc agagctctta tcgagtcgta agggaacaga                         220

<210> SEQ ID NO 18
<211> LENGTH: 220
<212> TYPE: DNA
<213> ORGANISM: Artificial sequence
<220> FEATURE:
<223> OTHER INFORMATION: TPALCAB capture molecule
<220> FEATURE:
<221> NAME/KEY: misc_feature
<222> LOCATION: (1)..(1)
<223> OTHER INFORMATION: aminated a
```

```
<400> SEQUENCE: 18
atgagtttca agatttcaac atgagtttca agatttcaac agcttctgat gttttccttg      60
aagagattaa gcccaaggag tttacatctt gattgtgttg ttcagcactt tgaacatggt     120
tggtcactgg attggctaaa aattgaagtt cagagcagta actagccatc cagagcagta     180
actagccatc gatgccgcct tgaatagcct cagcaagagt                           220

<210> SEQ ID NO 19
<211> LENGTH: 220
<212> TYPE: DNA
<213> ORGANISM: Artificial sequence
<220> FEATURE:
<223> OTHER INFORMATION: TPALRUBI capture molecule
<220> FEATURE:
<221> NAME/KEY: misc_feature
<222> LOCATION: (1)..(1)
<223> OTHER INFORMATION: aminated a

<400> SEQUENCE: 19
atgagtttca agatttcaac atgagtttca agatttcaac agcttctgat gttttccttg      60
aagagattaa gcccaaggag tttacatctt gattgtgttg ttcagcactt tgaacatggt     120
tggtcactgg attggctaaa aattgaagtt cagagcagta actagccatc cagagcagta     180
actagccatc taccgcgtag actcggcgat tgaactgtat                           220

<210> SEQ ID NO 20
<211> LENGTH: 60
<212> TYPE: DNA
<213> ORGANISM: Artificial sequence
<220> FEATURE:
<223> OTHER INFORMATION: ARBCL30 adaptor molecule

<400> SEQUENCE: 20
gtagcttacc ctttagacct ttttgaagaa tctgttccct tacgactcga taagagctct      60

<210> SEQ ID NO 21
<211> LENGTH: 60
<212> TYPE: DNA
<213> ORGANISM: Artificial sequence
<220> FEATURE:
<223> OTHER INFORMATION: ACAB30 adaptor molecule

<400> SEQUENCE: 21
ccaccacatc tgctactgca gtgctgaatg actcttgctg aggctattca aggcggcatc      60

<210> SEQ ID NO 22
<211> LENGTH: 60
<212> TYPE: DNA
<213> ORGANISM: Artificial sequence
<220> FEATURE:
<223> OTHER INFORMATION: ARUBI30 adaptor molecule

<400> SEQUENCE: 22
gacggcttct acattgcccc tgctttcatg atacagttca atcgccgagt ctacgcggta      60
```